United States Patent
Fritz et al.

(10) Patent No.: US 8,269,055 B2
(45) Date of Patent: Sep. 18, 2012

(54) METHOD FOR DEACTIVATION OF AN ORGANOMETALLIC CATALYST AND REACTOR SYSTEM THEREFOR

(75) Inventors: Peter Fritz, Unterhaching (DE); Heinz Bölt, Wolfratshausen (DE); Fuad Mosa, Riyadh (SA); Talal Ali, Riyadh (SA)

(73) Assignees: Saudi Basic Industries Corporation, Riyadh (SA); Linde AG, Munich (DE)

( * ) Notice: Subject to any disclaimer, the term of this patent is extended or adjusted under 35 U.S.C. 154(b) by 779 days.

(21) Appl. No.: 11/989,832

(22) PCT Filed: Jun. 13, 2006

(86) PCT No.: PCT/EP2006/005647
§ 371 (c)(1),
(2), (4) Date: Jun. 1, 2009

(87) PCT Pub. No.: WO2007/016997
PCT Pub. Date: Feb. 15, 2007

(65) Prior Publication Data
US 2009/0314986 A1 Dec. 24, 2009

(30) Foreign Application Priority Data
Jul. 29, 2005 (EP) ..................... 05016526

(51) Int. Cl.
*C07C 2/22* (2006.01)
(52) U.S. Cl. ........ 585/523; 585/502; 585/520; 585/521; 585/522

(58) Field of Classification Search .......... 585/502, 585/520, 521, 522, 523, 510, 511, 512
See application file for complete search history.

(56) References Cited

U.S. PATENT DOCUMENTS

| | | | | |
|---|---|---|---|---|
| 2,843,474 A * | 7/1958 | Ziegler et al. | ................. | 75/675 |
| 3,306,732 A * | 2/1967 | Toyoshima et al. | .............. | 75/675 |
| 4,396,788 A * | 8/1983 | Langer, Jr. | .................... | 585/523 |
| 4,486,615 A * | 12/1984 | Langer, Jr. | .................... | 585/523 |
| 5,371,053 A * | 12/1994 | Agapiou et al. | ................ | 502/56 |
| 5,750,816 A * | 5/1998 | Araki et al. | ................... | 585/512 |
| 5,811,619 A | 9/1998 | Commereric | | |
| 6,930,218 B2 | 8/2005 | Tempe | | |
| 2004/0199037 A1 * | 10/2004 | Kobayashi et al. | ........... | 585/502 |

OTHER PUBLICATIONS

Shilling, et al., "Heat Transfer Equipment" in Perry's Chemical Engineer's Handbook, 7th ed., R. H. Perry and D. W. Green, ed., McGraw-Hill, 1997, available on-line at www.knovel.com on Mar. 1, 2001.*

* cited by examiner

*Primary Examiner* — In Suk Bullock
*Assistant Examiner* — Bradley Etherton
(74) *Attorney, Agent, or Firm* — Kramer Levin Naftalis & Frankel LLP

(57) ABSTRACT

The present invention relates to a method for the deactivation of an organometallic catalyst in the product stream from an oligomerization reactor for the production of linear alpha-olefin, characterized in that the catalyst-containing product stream of the reactor is subjected to a temperature of at least 160° C. in a heating device. A reactor system for the method of the invention is also disclosed.

9 Claims, No Drawings

METHOD FOR DEACTIVATION OF AN ORGANOMETALLIC CATALYST AND REACTOR SYSTEM THEREFOR

The present invention relates to a method for deactivation of an organometallic catalyst utilized in a catalyzed process and a reactor system therefore.

Organometallic catalysts are widely utilized in homogenously and heterogenously catalyzed processes, such as the oligomerisation of ethylene, to obtain linear alpha-olefins.

For example, DE 43 38 414 C1 discloses a process for the production of linear alpha-olefins by oligomerizing of ethylene in the presence of an organic solvent and a homogenous catalyst. This process is carried out in an empty tubular reactor providing an outlet stream comprising solvent, catalyst, dissolved ethylene and linear alpha-olefins. As further activity of the catalyst in equipment parts following the process reactor shall be avoided, the catalyst has to be deactivated within a very short time period. This deactivation may be achieved according to the prior art by the addition of water, alcohol or fatty acid.

Additionally, DE 198 07 226 A1 discloses a process for deactivation of a catalyst wherein the active catalyst is mixed with a solution of a metal hydroxide in a protonic solvent, to quench the catalyst.

The methods for deactivation of an organometallic catalyst known in the prior art show the disadvantages that they require costly materials of construction, especially if caustic and water are applied, and also generate substantial amounts of inorganic wastes.

It is an object of the present invention to provide a method for deactivation of an organometallic catalyst utilized in a homogenously catalyzed process, which method overcomes the disadvantages of the prior art, especially providing a method avoiding cost intensive extraction systems and deactivation compounds together with substantial amounts of waste.

It is a further object of the present invention to provide a reactor system for carrying out the inventive method.

This object is achieved in that the catalyst-containing outlet stream of a process reactor is subjected to a temperature of at least 160° C. in a heating device.

Surprisingly, it was found that the organometallic catalyst utilized in a homogenously catalyzed process may be irreversibly deactivated by thermal treatment of the catalyst at a temperature of at least 160° C. Preferably, the catalyst is rapidly heated to that temperature.

Utilizing the method according to the present invention, cost-intensive extraction systems, such as caustic/water, are completely eliminated. Further, the waste generated is minimized and the catalyst components may be recovered.

Of course, the inventive method is applicable to all homogenously catalyzed reactions, such as oligomerization of ethylene, oxosynthesis and liquid phase polymerization, however its use in the oligomerization of ethylene is preferred.

Preferably, the catalyst comprises a zirconium salt of organic acids and at least one organoaluminum compound.

More preferably, the zirconium salt has the formula $ZrCl_{4-m}X_m$, wherein X=OCOR or $OSO_3R'$ with R and R' being independently alkyl, alkene or phenyl, and wherein 0<m<4.

In one embodiment, the at least one aluminum compound is $Al(C_2H_5)_3$, $Al_2Cl_3(C_2H_5)_3$ or $AlCl(C_2H_5)_2$.

Most preferably, the heating device is a thin film evaporator or a heat exchanger and a flash drum.

Further, the outlet stream may comprise solvent, catalyst, dissolved ethylene and linear alpha-olefins.

In this regard, the solvent may be selected from toluene, benzene and heptane, wherein toluene being preferred.

Further, it is preferred that the deactivated catalyst is separated from the outlet stream.

More preferably, the residence time of the catalyst-containing outlet stream in the heating device is from about 1 millisecond to about 1 minute.

Additionally, the object is achieved by a reactor system for catalyzed processes comprising a reactor and a heating device connected thereto to heat a catalyst-containing outlet stream of the reactor to a temperature of at least 160° C.

Finally, it is preferred that the heating device is a thin film evaporator or a heat exchanger and a flash drum.

Additional features and advantages of the inventive method will become apparent from the following detailed description of an exemplary embodiment of the inventive method in the process of oligomerisation of ethylene.

In the process of oligomerisation of ethylene to obtain linear alpha-olefins ethylene is oligomerized in a reactor in the presence of a solvent and a homogenous organometallic catalyst. From the oligomerisation reactor is preferably taken via a first line. a mixture of ethylene and light alpha-olefins, together with some toluene which has been used as solvent. Via a second line a liquid mixture of toluene, catalyst, dissolved ethylene and linear alpha-olefins is discharged. To avoid further activity of the catalyst in the equipment parts following the oligomerisation reactor, it is essential to deactivate the catalyst as soon as possible. According to the inventive method this is achieved by subjecting this catalyst-containing outlet stream from the oligomerisation reactor to a temperature of at least 160° C. in a heating device. Preferably, such a heating device may be a thin film evaporator or a heat exchanger and a flash drum which are able to heat the outlet stream rapidly to the desired temperature. At this temperature, the active catalytic components contained in the outlet stream are irreversibly destructed.

Thus, the inventive reactor system comprises a reactor and a heating device connected thereto, so that the catalyst-containing outlet stream from the reactor may be transferred into the heating device to heat the outlet stream to a temperature of at least 160° C. Most preferably, the residence time of the outlet stream in the heating device is from about 1 millisecond to about 1 minute.

It was found that the linear alpha olefins also present in the outlet stream are stable in a temperature range of 60 to about 300° C., so that the treatment of the outlet stream at a temperature of at least 160° C. is not detrimental for the linear-alpha olefins to be obtained.

After heat treatment in the heating device, the outlet stream now containing deactivated catalyst components may be further processed according to the prior art processes, i.e. the catalyst components may be separated from the outlet stream and the linear alpha-olefins may be fractionated.

The features disclosed in the foregoing description or in the claims may, both separately and in any combination thereof, be material for realizing the invention in diverse forms thereof.

The invention claimed is:

1. A method for the deactivation of a catalyst comprising a zirconium salt of organic acids and an organoaluminum compound comprising $Al_2Cl_3(C_2H_5)_3$ or $AlCl(C_2H_5)_2$ in the oligomer product stream from an oligomerization reactor for the production of linear alpha-olefin, characterized in that the catalyst-containing oligomer product stream of the reactor is raised to a temperature of at least 160° C.

2. The method according to claim 1, wherein the oligomerization reaction is the homogenously catalyzed oligomerization of ethylene.

3. The method according to claim 2, wherein the product stream is raised to a temperature of 160° C. in a heating device comprising a thin film evaporator or a heat exchanger which discharges the heated product stream into a flash drum.

4. The method according to claim 3, wherein the residence time of the catalyst-containing product stream in the heating device is from about 1 millisecond to about 1 minute.

5. The method according to claim 4, wherein the zirconium salt has the formula $ZrCl_{4-m}X_m$, wherein X=OCOR or $OSO_3R'$ and R and R' are independently alkyl, alkene or phenyl, and $0<m<4$.

6. The method according to claim 5, wherein the product stream is raised to a temperature of 160° C. in a thin film evaporator or a heat exchanger which discharges the heated product stream into a flash drum.

7. The method according to claim 6, wherein the residence time of the catalyst-containing product stream in the heating device is from about 1 millisecond to about 1 minute.

8. The method according to claim 2, wherein the product stream comprises the solvent, the catalyst, dissolved ethylene and linear alpha-olefins.

9. The method according to claim 8, wherein the solvent is selected from toluene, benzene and heptane.

* * * * *